United States Patent

Hefner, Jr. et al.

[11] Patent Number: 5,264,502
[45] Date of Patent: Nov. 23, 1993

[54] DIAMINO-ALPHA-ALKYLSTILBENE CURING AGENTS FOR EPOXY RESINS

[75] Inventors: Robert E. Hefner, Jr.; Jimmy D. Earls, both of Lake Jackson, Tex.

[73] Assignee: The Dow Chemical Company, Midland, Mich.

[21] Appl. No.: 684,082

[22] Filed: Apr. 10, 1991

Related U.S. Application Data

[63] Continuation-in-part of Ser. No. 562,289, Aug. 3, 1990.

[51] Int. Cl.⁵ .................. C08L 63/02; C08L 63/04
[52] U.S. Cl. ...................... 525/529; 525/486; 525/511; 525/524; 525/525; 525/526; 525/527; 558/411; 564/305; 564/307; 564/441; 564/442; 564/443
[58] Field of Search ............... 525/511, 524, 525, 526, 525/527, 529, 486; 558/411; 564/305, 307, 441, 442, 443

[56] References Cited

U.S. PATENT DOCUMENTS

| | | | |
|---|---|---|---|
| 2,537,950 | 1/1951 | Allen | 260/578 |
| 2,712,001 | 6/1955 | Owen | |
| 3,004,951 | 10/1961 | Dazzi | |
| 3,133,033 | 5/1964 | St. Clair et al. | |
| 3,291,775 | 12/1966 | Holm | |
| 3,373,140 | 3/1968 | Aftergut | 260/47 |
| 3,374,203 | 3/1968 | Schmukler | |
| 3,378,525 | 4/1968 | Sellers | |
| 3,386,953 | 6/1968 | Dunnlag et al. | |
| 3,484,408 | 12/1969 | Holm | |
| 3,774,305 | 11/1973 | Stoffey et al. | 32/15 |
| 3,784,516 | 1/1974 | Baxter et al. | |
| 3,907,768 | 9/1975 | van der Veen et al. | |
| 3,919,317 | 11/1975 | Huff et al. | |
| 4,027,950 | 6/1977 | Moriyama et al. | 350/160 LC |
| 4,045,408 | 8/1977 | Griffith et al. | |
| 4,072,656 | 2/1978 | Hartmann | |
| 4,153,621 | 5/1979 | Hartmann | 528/109 |
| 4,349,619 | 9/1982 | Kimoshida et al. | 430/196 |
| 4,499,255 | 2/1985 | Wang et al. | 525/507 |
| 4,594,291 | 6/1986 | Bertram et al. | 525/485 |
| 4,595,761 | 6/1986 | Chattha | 562/440 |
| 4,609,719 | 9/1986 | Chattha | 528/98 |
| 4,611,046 | 9/1986 | Chattha | 528/98 |
| 4,611,047 | 9/1986 | Chattha | 528/114 |
| 4,636,535 | 1/1987 | Wang et al. | 525/523 |
| 4,645,803 | 2/1987 | Kohli et al. | 525/524 |
| 4,663,401 | 5/1987 | Saito et al. | 525/523 |
| 4,717,674 | 1/1988 | Sung | 436/85 |
| 4,745,135 | 5/1988 | Thomas et al. | 525/130 |
| 4,745,136 | 5/1988 | Thomas et al. | 525/130 |
| 4,745,137 | 5/1988 | Thomas et al. | 525/130 |
| 4,762,901 | 9/1988 | Dhein et al. | 528/73 |
| 4,764,581 | 8/1988 | Mueller et al. | 528/100 |
| 4,791,154 | 12/1988 | Corley et al. | 523/456 |

FOREIGN PATENT DOCUMENTS

| | | |
|---|---|---|
| 0252358 | 1/1988 | European Pat. Off. |
| 0379055 | 1/1990 | European Pat. Off. |
| 0379057 | 1/1990 | European Pat. Off. |
| 4217660 | 5/1964 | Japan |
| 56-152830 | 11/1980 | Japan |
| 56-26849 | 3/1981 | Japan ............ 564/305 |
| 58-206579 | 5/1982 | Japan |
| 62-96484 | 5/1987 | Japan |
| 63-10617 | 1/1988 | Japan |
| 1170105 | 2/1967 | United Kingdom |

OTHER PUBLICATIONS

Chem. Abst. 60:5407g (Roczniki Chem., 37(9), pp. 1085–1087, 1963).
Chem. Abst. 90:138566d (Pol. Patent 97,557).
Chem. Abst. 92:59604c (Vysokomol. Soedin., Ser. B, 21(10), pp. 780–783, 1979).
Chem. Abst. 95:97564j (Pol. Patent 107,754).
Chem. Abst. 95:116389z (Polym. Bull. (Berlin), 4(8), pp. 479–485, 1981).

(List continued on next page.)

Primary Examiner—Robert E. Sellers

[57] ABSTRACT

An epoxy resin composition useful as a molded article is cured with a combination of curing agents including diamino-alphaalkylstilbenes and other curing agents wherein the epoxy resin and/or the other curing agent can contain rodlike mesogenic moieties.

10 Claims, No Drawings

OTHER PUBLICATIONS

Derwent: 89-110662 New Epoxy! Resin Comp.–used to seal semiconductor devices.

"Note a Photocrosslinkable Vinyl Polyester" by Sadafule et al. in *J. Mac. Sci.-Chem.*, A25(1), pp. 121–126 (1988).

Varma and Kothari in *Indian Journal of Technology*, vol. 21, pp. 265–267 (Jul. 1983).

Eichler and Mleziva in *Die Angewandte Makromolekulare Chemie*, vol. 19, #239, pp. 31–55 (1971).

Dobas and Eichler in Faserforshung und Textiltechnik, *Zeitschrift fur Polymerforschung*, 28, 11/12, pp. 589–594 (1977).

Chattha, Cassatta and Siegl in *Journal of Applied Polymer Science*, 33, pp. 1829–1834 (1987).

"Studies in the Photodimerization of the Diglycidyl Ether of 4,4'-Dihydroxychalcone" by Zahir, *J. App. Pol. Sc.*, vol. 23 pp. 1355–1372 (1975).

"Photocrosslinkable Resins with Benzylidene-acetophenone (Chalcone) Structure in the Repeat Units" by Panda, *J. Pol. Sc.*, vol. 13, pp. 1757–1764 (1975).

*J. Appl. Polym. Sci.*, Chattha et al, 1987, 33(5), 1829–1834.

Chem. Abst. 101:24301d (*Vysokomol. Soedin., Ser. A*, Sierocka et al, 1984, 26(2), 250–6.

Chem. Abst. 101:192592t (Eur. Polym. J., Sek, 1984 20(8), 805–9.

Chem. Abst. 104:6259d (lsv. Sev.-Kavk. Nauchn. Tsentra Vyssh Shk., Estestv. Nauki, Mokaeva et al, 1984, (4), 63–5.

Chem. Abst. 106:52298e (Japan. Kokai Tokkyo Koho JP 60 58,481).

Derwent 59720a/33 (J53 079998).

Derwent 61196w/37 (J5 0052–039).

Derwent 90978y/51 (J52 133885).

Derwent 84-004219/01 (SU 998946-A).

*ACS Symposium Series* 114, Chapter 17, pp. 259–262, (given Sep. 1978, at the 176th meeting of the American Chemical Society by James R. Griffith.

DIAMINO-ALPHA-ALKYLSTILBENE CURING AGENTS FOR EPOXY RESINS

CROSS-REFERENCE TO RELATED APPLICATIONS

This application is a continuation-in-part of application Ser. No. 07/562,289 filed Aug. 3, 1990, now pending, which is incorporated herein by reference in its entirety.

FIELD OF THE INVENTION

The present invention concerns diamino-alphaalkylstilbene compositions, curable (thermosettable) mixtures thereof with one or more epoxy resins, as well as the cured (thermoset) compositions thereof.

BACKGROUND OF THE INVENTION

Epoxy resins are a well established class of curable (thermosettable) compositions which find utility in a myriad of applications. The curing of epoxy resins is effected by a wide range of curing agents, for example, the primary and secondary polyamines including the aliphatic amines, cycloaliphatic amines and aromatic amines; dicarboxylic acids and anhydrides thereof; aromatic hydroxyl containing compounds; imidazoles; guanidines; urea-aldehyde resins, melamine-aldehyde resins and alkoxylated derivatives thereof; amidoamines and various combinations thereof. In many of the applications served by epoxy resins, it would be desirable to improve one or more of the physical and/or mechanical and/or thermal properties of the cured products.

The present invention provides diamino-alphaalkylstilbene compositions which are useful for curing epoxy resins. Certain of these compositions, notably the 4,4'-diamino-alpha-alkylstilbenes and the N,N'-dialkyl-4,4'-diamino-alpha-alkylstilbenes, are mesogenic. The aforesaid mesogenic diamino-alphaalkylstilbenes, when combined with certain epoxy resins, for example, the diglycidyl ether of 4,4'-dihydroxyalpha-methylstilbene, exhibit ordering of the molecular chains in the melt phase. This morphology is susceptible to flow induced orientation during processing which can result in enhanced unidirectional mechanical properties. Rigidity imparted to the thermoset matrix by the rigid rodlike, mesogenic structure can additionally result in enhanced thermal stability. This is not possible to attain to any significant extent with conventional (non-mesogenic) diamine curing agent and epoxy resin compositions.

The term "mesogenic" as is used herein designates compounds containing one or more rigid rodlike structural units which have been found to favor the formation of liquid crystal phases in the case of low molar mass substances. Thus the mesogen or mesogenic moiety is that structure responsible for molecular ordering.

SUMMARY OF THE INVENTION

One aspect of the present invention pertains to diamino-alpha-alkylstilbenes represented by the following Formula I

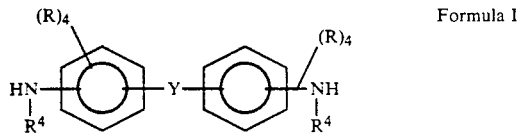
Formula I wherein each R is independently hydrogen or a hydrocarbyl or hydrocarbyloxy group having from 1 to about 10, preferably 1 to about 4, carbon atoms, a halogen atom, preferably chlorine or bromine, a nitro group, a nitrile group, a phenyl group or a $-CO-R^1$ group; each $R^1$ is independently hydrogen or a hydrocarbyl group having from 1 to about 3 carbon atoms; each $R^4$ is independently hydrogen or a hydrocarbyl group having from 1 to about 10, preferably 1 to about 6, carbon atoms; Y is a

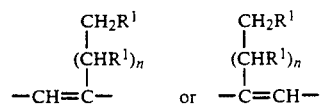

group and n has a value of zero or one.

Another aspect of the present invention pertains to curable (thermosettable) compositions comprising (A) a curing amount of one or more diaminoalpha-alkylstilbenes and (B) one or more epoxy resins.

Another aspect of the present invention pertains to curable (thermosettable) compositions comprising (A) a curing amount of one or more diaminoalpha-alkylstilbenes and (B) one or more advanced epoxy resins.

A further aspect of the present invention pertains to products resulting from curing the aforementioned curable compositions.

A further aspect of the present invention pertains to products resulting from the application of an electric field or magnetic field or drawing and/or shear flow before and/or during curing or processing of the aforementioned curable compositions.

DETAILED DESCRIPTION OF THE INVENTION

Diamino-alpha-alkylstilbene compositions of the present invention can be prepared by reacting the corresponding dihydroxy-alpha-alkylstilbene compound represented by the following Formula II

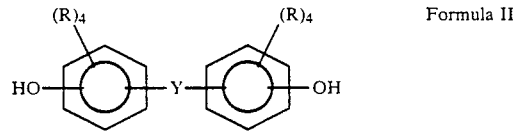
Formula II wherein, R, $R^1$, Y and n are as hereinbefore defined with a 4-halo-2-arylquinazoline to provide the corresponding bis(4-aryloxy-2-arylquinazoline) of the dihydroxy-alphaalkylstilbene. The resultant bis(aryloxyquinazoline) is then subjected to conditions which lead to thermally induced rearrangement to the corresponding bis(3-aryl-2aryl-4(3H)quinazolinone. Hydrolysis of the bis(3-aryl-2-aryl-4(3H)quinazolinone provides the corresponding diamino-alpha-alkylstilbene. Details concerning the aforementioned reaction sequence are given by Scherrer and Beatty in The Journal of Organic Chemistry, volume 37, number 11, pages 1681 to 1686 (Jun. 2, 1972) which is incorporated herein by reference. Additional general methodology for the conversion of the phenolic hydroxyl group to the aniline amino group is given by Rossi and Bunnett in The Journal of Organic Chemistry, volume 37, number 19, page 3570 (1972).

To prepare certain aryl substituted diaminoalpha-alkylstilbene compositions (Formula I where at least one R is other than hydrogen) care must be taken that substituents are stable at the temperature required for the thermally induced rearrangement step and conditions required for the hydrolysis step. Substituents which would not survive conditions required for the two aforementioned steps may conveniently be incorporated into the unsubstituted (or partially substituted) diamino-alpha-alkylstilbene product. When chemistry to incorporate said substituents is to be practiced, it is frequently of value to protect the amine functionalities prior to substitution reaction followed by deprotection to regenerate the free amine groups. General methodology for the protectiondeprotection of the amine group is well established, for example, as reported by Greene in *Protective Groups in Organic Synthesis* published by Wiley-Interscience, New York (1981) and incorporated herein by reference.

Methods for use in preparing N-substituted diamino-alpha-alkylstilbene compositions (Formula I where at least one $R^4$ is other than hydrogen) may be adapted from the techniques given by Sandler and Karo in *Organic Functional Group Preparations* published by Academic Press, Inc., New York (1983) on pages 387 to 390 and incorporated herein by reference. As an example of the use of the methods reported therein, 4,4'-diamino-alpha-methylstilbene (Formula I where $R=-H$, $R^4=-H$ and $Y=$

as $R^1=-H$ and $n=0$) is converted to 4,4'-diacetamido-alpha-methylstilbene followed by N-methylation to provide N,N'-dimethyl-4,4'-diacetamido-alphamethyl-stilbene. Hydrolytic cleavage of the acetamido groups yields the desired N,N'-dimethyl-4,4'-diaminoalpha-methylstilbene (Formula I where $R=-H$, $R^4=-CH_3$ and $Y=$

as $R^1=-H$ and $n=0$)

EPOXY RESIN COMPONENT

Suitable epoxy resins which can be employed herein to prepare the curable compositions of the present invention include essentially any epoxycontaining compound which contains an average of more than one vicinal epoxide group per molecule. The epoxide groups can be attached to any oxygen, sulfur or nitrogen atom or the single bonded oxygen atom attached to the carbon atom of a —CO—O— group in which said oxygen, sulfur or nitrogen atom or the carbon atom of the —CO—O— group is attached to an aliphatic, aromatic or cycloaliphatic hydrocarbon group which hydrocarbon group can be substituted with any inert substituent including, but not limited to, halogen atoms, preferably chlorine or bromine, nitro groups and the like or such groups can be attached to the terminal carbon atoms of a compound containing an average of more than one —(O—CHR$^a$—CHR$^a$—)t group where each R$^a$ is independently hydrogen or an alkyl or haloalkyl group, containing from 1 to about 2 carbon atoms, with the proviso that only one R$^a$ group can be a haloalkyl group, and t has a value from 1 to about 100, preferably from 1 to about 20, more preferably from 1 to about 10, most preferably from 1 to about 5.

Particularly suitable epoxy resins which can be employed herein include those compounds having an average of more than one vicinal epoxide group per molecule, such as, for example, the glycidyl ethers or glycidyl amines represented by the following Formulas III, IV, V, VI, VII, VIII, IX, X or XI

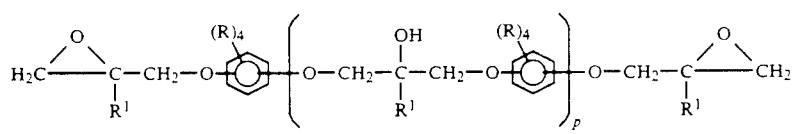

Formula III

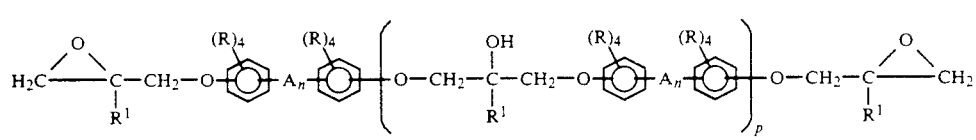

Formula IV

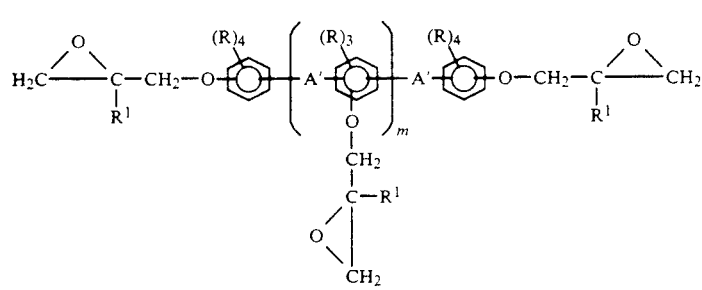

Formula V

-continued

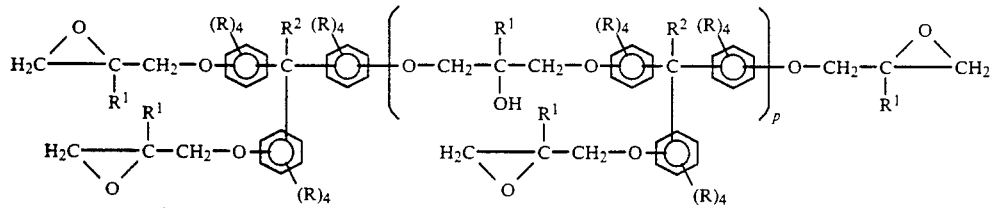
Formula VI

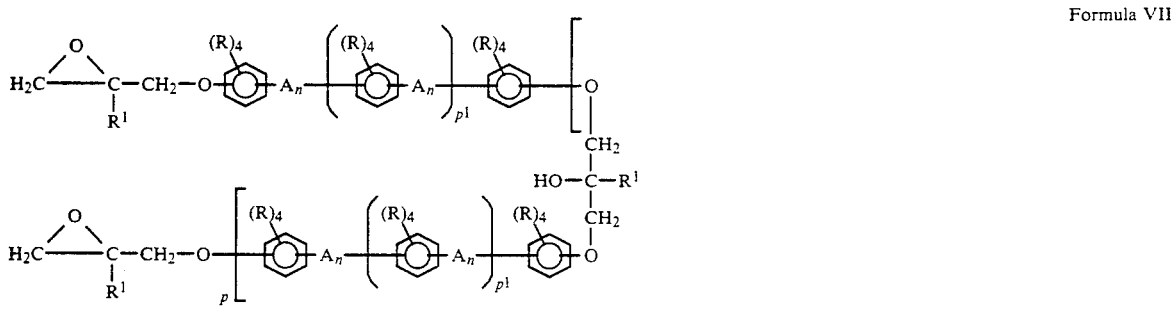
Formula VII

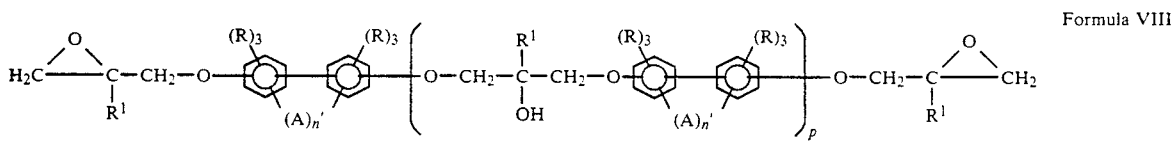
Formula VIII

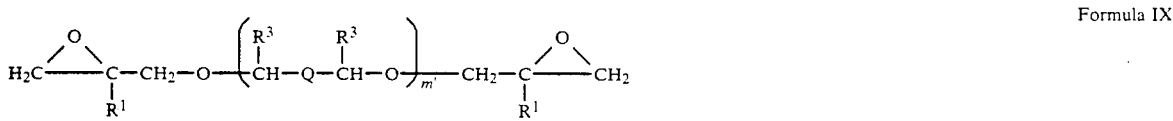
Formula IX

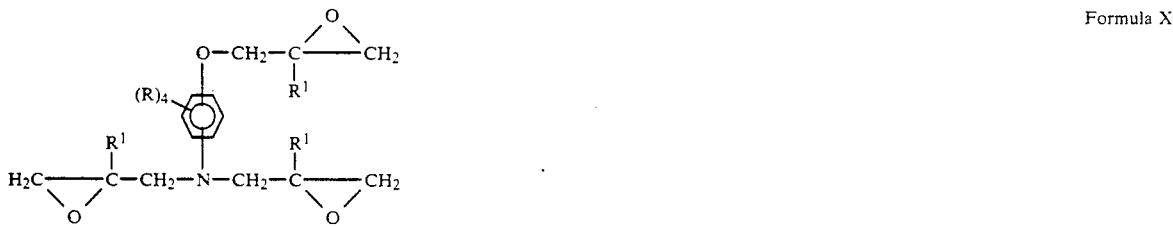
Formula X

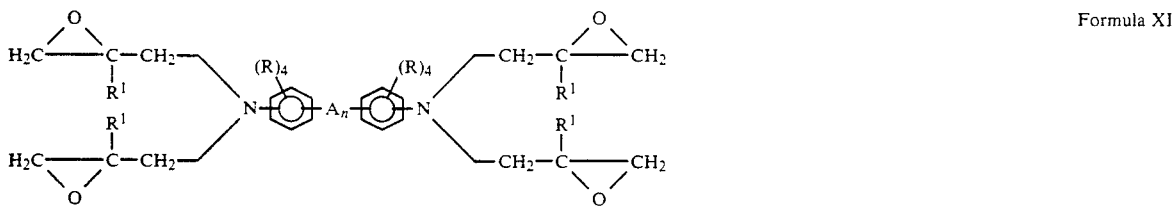
Formula XI wherein R, $R^1$ and n are as hereinbefore defined; each A is independently a direct single bond, a divalent saturated aliphatic hydrocarbyl group having from 1 to about 20, preferably from 1 to about 14, carbon atoms, —O—, —CO—, —SO—, —SO$_2$—, —S—, —S—S—, —CR$^1$=CR$^1$, —C≡C—, —N=N—, —CR$^1$=N—, —O—CO—, —NR$^1$—CO—, —CR$^1$=N—N=CR$^1$—, —CR$^1$=CR$^1$—CO—, —N=CR$^1$—, —CO—O—, —CO—NR$^1$—, —CO—CR$^1$=CR$^1$—, —CO—O—N=CR$^1$—, —CR$^1$=N—O—OC—, —CO—NR$^1$—NR$^1$—OC—, —CR$^1$=CR$^1$—O—OC—, —CO—O—CR$^1$=CR$^1$—, —O—OC—CR$^1$=CR$^1$—, —CR$^1$=CR$^1$—CO—O—, —(CHR$^1$)$_{n'}$—O—CO—CR$^1$=CR$^1$—, $R^1$—CO—O—(CHR$^1$)$_{n'}$—, —(CHR$^1$)$_{n'}$—CO—O—CR$^1$=CR$^1$—, —CR$^1$=C-, —CR$^1$=C-, $R^1$—O—CO—(CHR$^1$)$_{n'}$—, —CO—S—, —S—OC—, —CH$_2$—CH$_2$—CO—O—, —O—OC—CH$_2$—CH$_2$—, —C≡C—C≡C—, —CR$^1$=CR$^1$—CR$^1$=CR$^1$—,

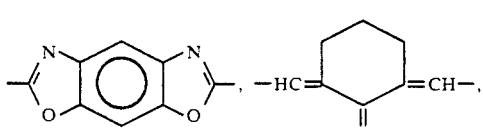

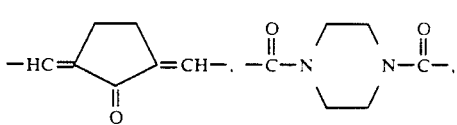

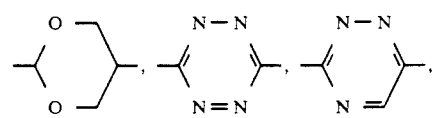
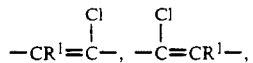
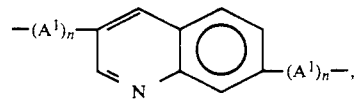
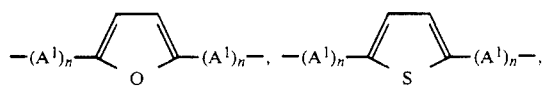
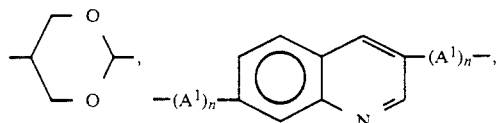
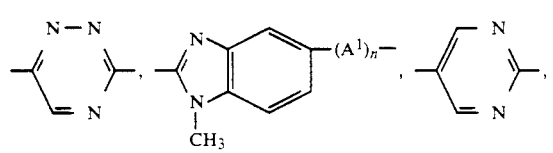
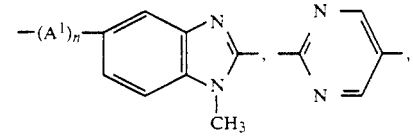
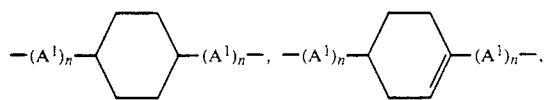
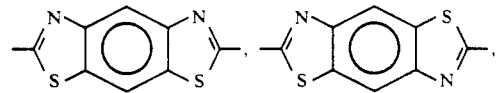
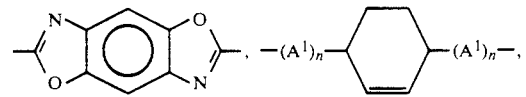
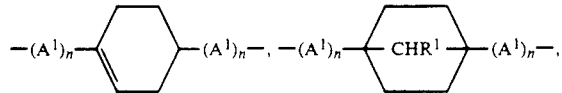
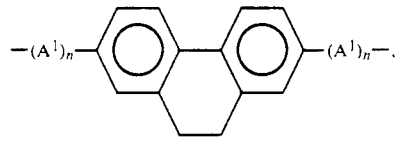

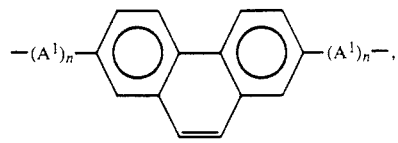
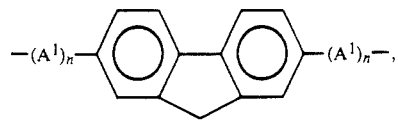
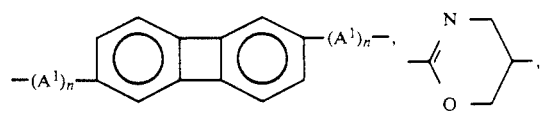
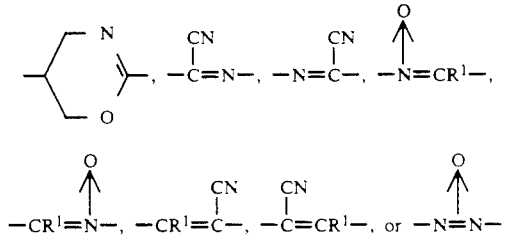
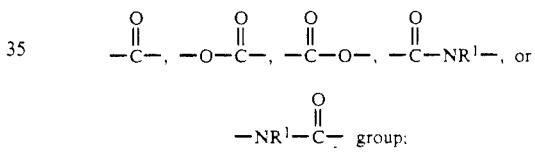

each A' is independently a divalent hydrocarbyl group having from 1 to about 10, preferably from 1 to about 4, carbon atoms; each $A^1$ is independently a

group;

each $R^2$ is independently hydrogen or a hydrocarbyl group having from 1 to about 10, preferably from 1 to about 3, carbon atoms, a halogen atom, preferably chlorine or bromine; each $R^3$ is independently hydrogen or a hydrocarbyl or halohydrocarbyl group having from 1 to about 6, preferably 1 to about 2 carbon atoms; Q is a direct bond, $-CH_2-S-CH_2-$, $-(CH_2)_{n''}-$, or

[hexagon with S]

m has a value from about 0.001 to about 6, preferably from about 0.01 to about 3; m' has a value from 1 to about 10, preferably from about 1 to about 4; p has a value from zero to about 30, preferably from zero to about 5; n' has a value from 1 to about 6, preferably 1 to about 3; n'' has an average value from about 1 to about 10; and $p^1$ has a value from 1 to about 30, preferably from 1 to about 3. The aromatic rings can also contain one or more heteroatoms selected from N, O, S and the like.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic or cycloaliphatic groups can be saturated or unsaturated. When applied to the A' group of Formula VIII, the hydrocarbyl group can also contain one or more heteroatoms selected from N, O, S and the like. Likewise, the term hydrocarbyloxy means a hydrocarbyl group having an oxygen linkage between it and the carbon atom to which it is attached.

Representative of the polyepoxide compounds which are free of mesogenic or rodlike moieties include, for example, the diglycidyl ethers of resorcinol, 4,4'-isopropylidenediphenol (bisphenol A), 4,4'-dihydroxybenzophenone (bisphenol K), 1,1-bis(4-hydroxyphenyl)-1-phenylethane (bisphenol AP), dihydroxydiphenylmethane (bisphenol F), 3,3',5,5'-tetrabromobisphenol A, 4,4'-thiodiphenol (bisphenol S), 4,4'-sulfonyldiphenol, 4,4'-dihydroxydiphenyl oxide, 3-phenylbisphenol A, 3,3'5,5'-tetrachlorobisphenol A, 3,3'-dimethoxybisphenol A, dipropylene glycol, poly(propylene glycol)s, thiodiglycol; the triglycidyl ether of tris(hydroxyphenyl)methane; the triglycidyl ether of p-aminophenol; the tetraglycidyl ether of 4,4'-diaminodiphenylmethane; the polyglycidyl ether of a phenol or substituted phenol-aldehyde condensation product (novolac); the polyglycidyl ether of a dicyclopentadiene or an oligomer thereof and phenol or substituted phenol condensation product; the advancement reaction products of the aforesaid di- and polyglycidyl ethers with aromatic di- or polyhydroxyl- or di- or polycarboxylic acid containing compounds including, for example, bisphenol A (4,4'-isopropylidenediphenol), o-, m-, p-dihydroxybenzene, 2,4-dimethylresorcinol, 4chlororesorcinol, tetramethylhydroquinone, 1,1-bis(-4hydroxyphenyl)ethane, bis(4,4'-dihydroxyphenyl)methane, 4,4'-dihydroxydiphenyl ether, 3,3',5,5'-tetramethyldihydroxydiphenyl ether, 3,3',5,5'-dichlorodihydroxydiphenyl ether, 4,4'-bis(p-hydroxyphenylisopropyl)diphenyl ether, 4,4'-bis(p-hydroxyphenoxy)benzene, 4,4'-bis(p-hydroxyphenoxy)diphenyl ether, 4,4'-bis(4(4-hydroxyphenoxy)phenyl sulfone)diphenyl ether, 4,4'-dihydroxydiphenyl sulfone, 4,4'-dihydroxydiphenyl sulfide, 4,4'-dihydroxydiphenyl disulfide, 2,2'-dihydroxydiphenyl sulfone, 4,4'-dihydroxydiphenyl methane, 1,1-bis(p-hydroxyphenyl)cyclohexane, 4,4'-dihydroxybenzophenone, phloroglucinol, pyrogallol, 2,2',5,5'-tetrahydroxydiphenyl sulfone, tris(hydroxyphenyl)methane, dicyclopentadiene diphenol, tricyclopentadiene diphenol, terephthalic acid, isophthalic acid, p-hydroxybenzoic acid; mixtures thereof and the like.

The epoxy resins containing a mesogenic or rodlike moiety which can particularly be employed herein include, for example, those represented by the aforementioned Formulas IV, VII, VIII or XI wherein at least 80 percent of the molecules are para substituted by both the bridging groups (—A—) and the substituent containing the glycidyl group(s)

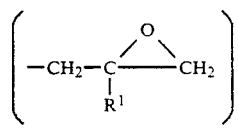

as well as the substituent containing the secondary hydroxy alkylidene group(s)

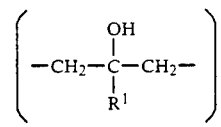

which are present when p or $p^1$ has a value greater than zero. For Formula VIII, it is to be understood that para substitution is with respect to the direct bond between the aromatic rings.

The bridging groups (—A—) in the formulas for the epoxy resins containing mesogenic or rodlike moieties form a rigid central linkage between the aromatic ring pairs, that is, A is a direct single bond, —C≡C—, —CR$^1$=N—, —N=N—, —O—CO—, —NR$^1$—CO—, —CR$^1$=N—N=CR$^1$—, —CR$^1$=CR$^1$—CO—, —CR$^1$=CR$^1$—, —N=CR$^1$—, —CO—O—, —CO—NR$^1$—, —CO—CR$^1$=CR$^1$—, —CO—O—N=CR$^1$—, —CR$^1$=N—O—OC—, —CO—NR$^1$—NR$^1$—OC—, —CR$^1$=CR$^1$—O—OC—, —CO—O—CR$^1$=CR$^1$—, —O—OC—CR$^1$=CR$^1$—, —CR$^1$=CR$^1$—CO—O—, —(CHR$^1$)$_{n'}$—O—CO—CR$^1$=CR$^1$—, —CR$^1$=CR$^1$—CO—O—(CHR$^1$)$_{n'}$—, —(CHR$^1$)$_{n'}$—CO—O—CR$^1$=CR$^1$—, —CR$^1$=CR$^1$—O—CO—(CHR$^1$)$_{n'}$—, —CO—S—, —S—OC—, —CH$_2$—CH$_2$—CO—O—, —O—OC—CH$_2$—CH$_2$—, —C≡C—C≡C—, —CR$^1$=CR$^1$—CR$^1$=CR$^1$—,

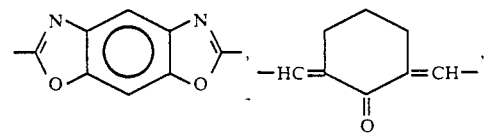

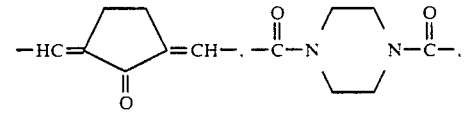

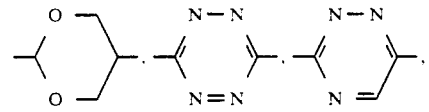

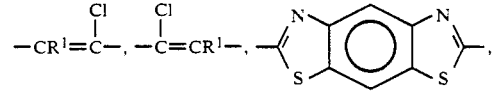

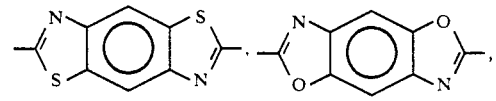

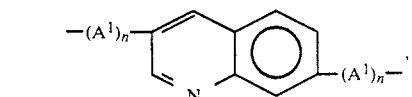

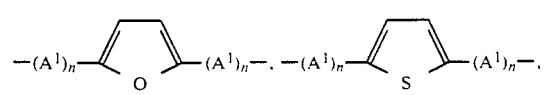

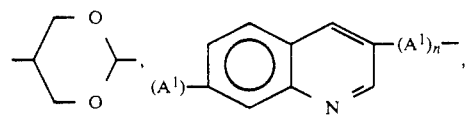
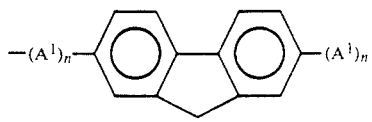
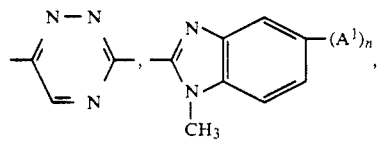
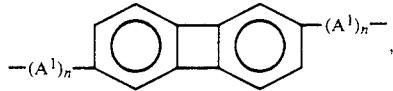
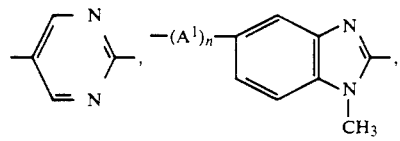
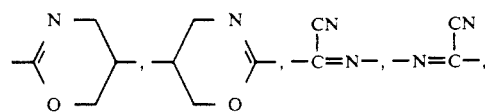
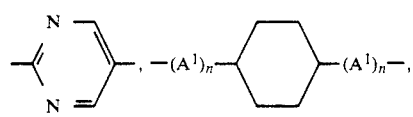
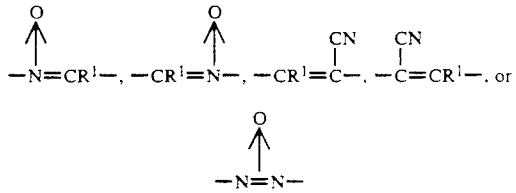
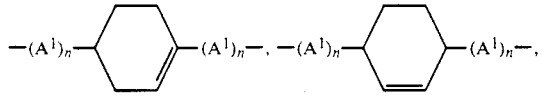
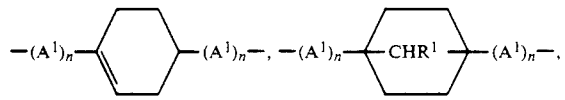
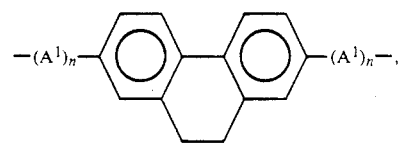
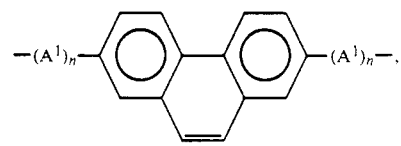

group and n, $A^1$ and $R^1$ are as hereinbefore described. To optimize the aspect ratio of said mesogenic or rodlike functionalities, it is preferred that the aromatic ring substituents (R in Formulas IV, VII, VIII and XI) are hydrogen or methyl groups.

Representative polyepoxide compounds containing a mesogenic or rodlike moiety include, for example, the diglycidyl ethers of 4,4'-dihydroxybiphenyl, 4,4'-dihydroxystilbene, 4,4'-dihydroxydiphenylacetylene, 4,4'-dihydroxydiphenylazomethine, 4,4'-dihydroxyazobenzene, 4,4'-dihydroxyazoxybenzene, 4,4'-bis((4-hydroxy)phenoxy)diphenyl, 4,4'-dihydroxy-alphamethylstilbene, 3,3',5,5'-tetramethyl-4,4'-dihydroxydiphenyl, 3,3',5,5'-tetrachloro-4,4'-dihydroxydiphenyl, 2,2',6,6'-tetramethyl-4,4'-dihydroxydiphenyl, 4,4'-dihydroxybenzanilide, 4,4'-dihydroxychalcone, 4,4'-dihydroxy-alpha-cyanostilbene, 4-hydroxyphenyl-4hydroxybenzoate, 4,4'-dihydroxy-3,3',5,5'-tetrabromoalpha-methylstilbene, N,N'-bis(4-hydroxyphenyl)terephthalamide, the diglycidyl ethers of the dihydric phenols represented by the following formulas:

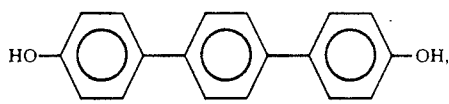
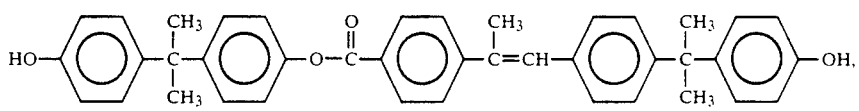
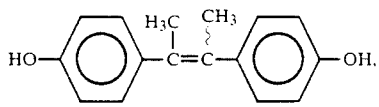

-continued
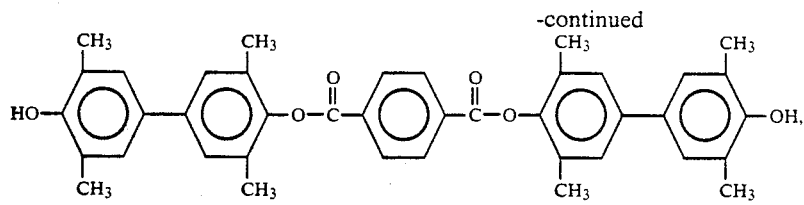
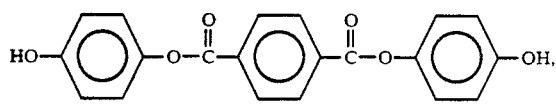
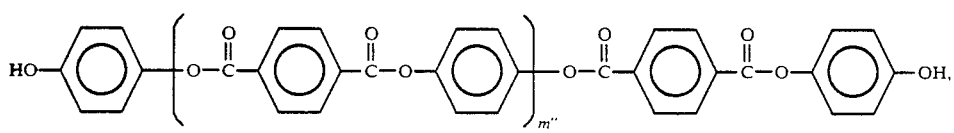
where m" has a value from 1 to about 10
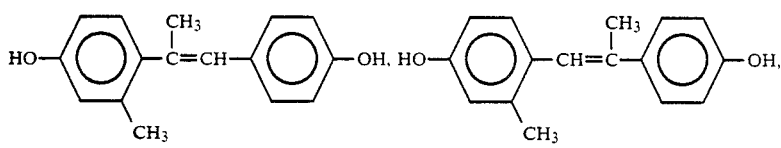
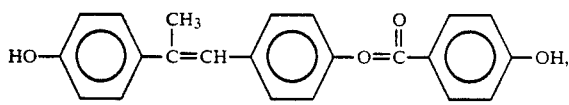
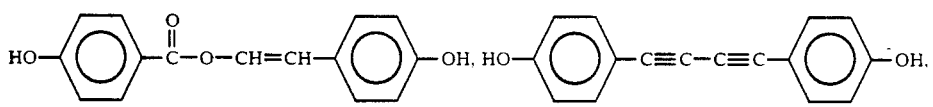
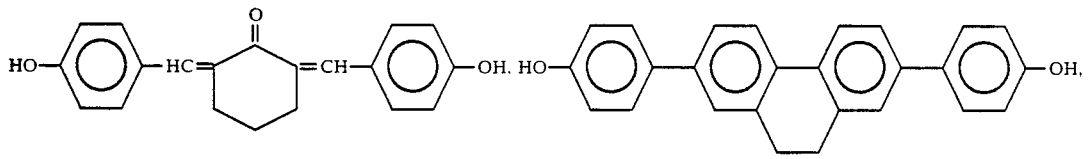
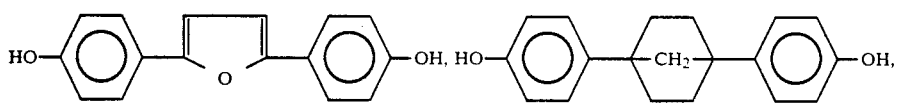
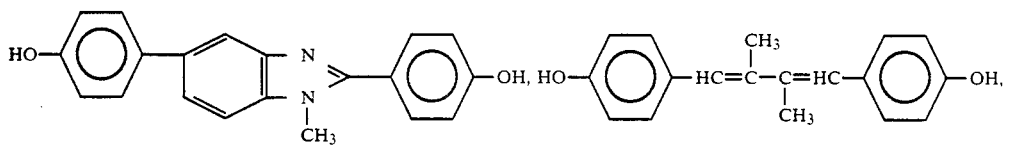
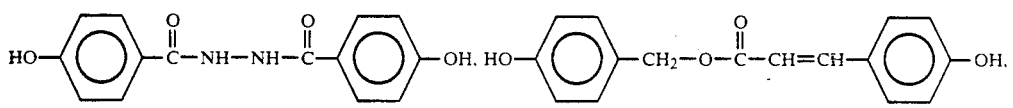

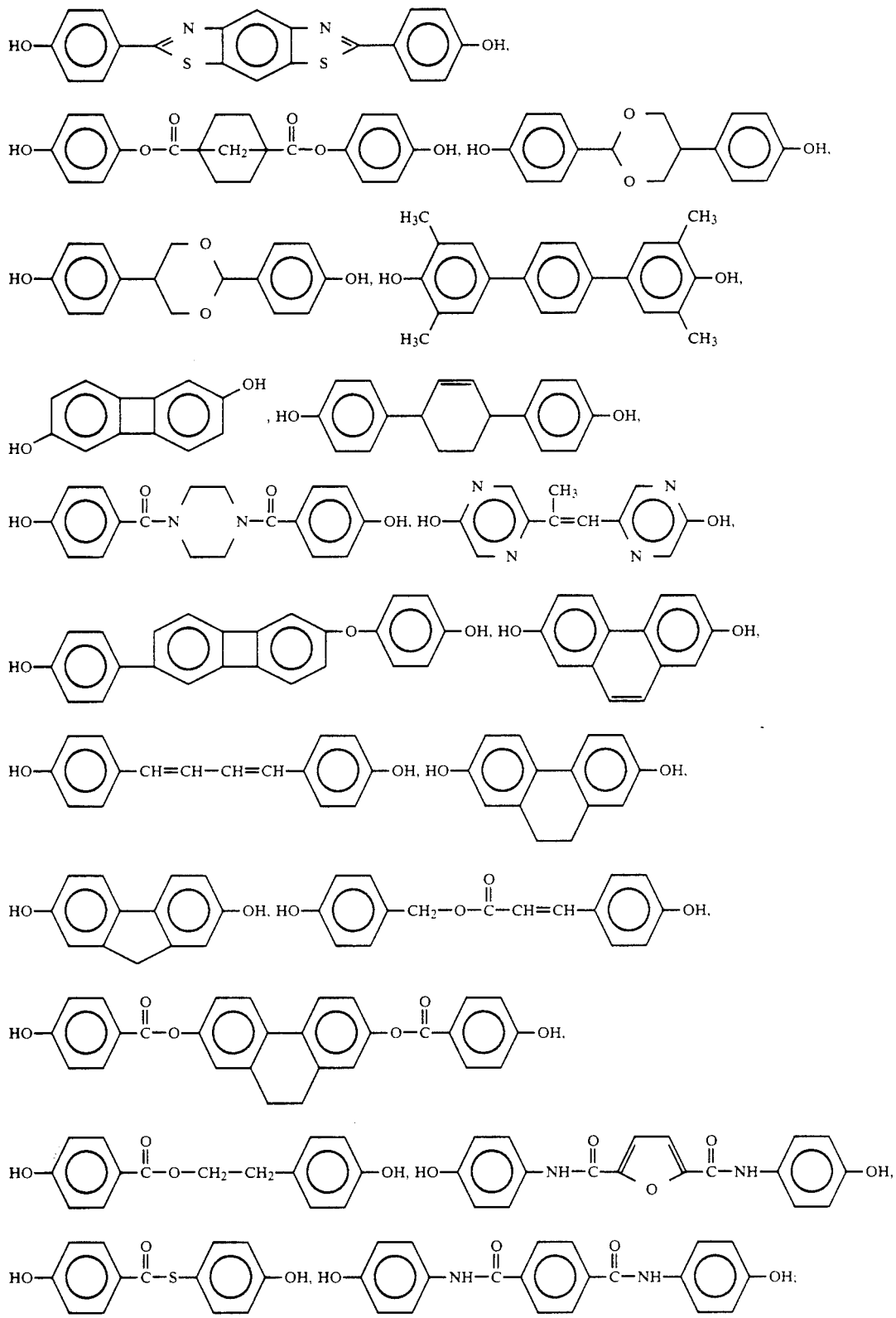

the tetraglycidyl amines of 4,4'-diamino-alphamethylstilbene, 4,4'-diaminostilbene, 4,4'-diaminobenzanilide, 4,4'-diaminoazobenzene, 4,4'-diamino-alpha-cyanostilbene. Also suitable are the products resulting from advancing the aforementioned diglycidyl ethers with aromatic dihydroxyl or dicarboxylic acid containing compounds including, for example, all of the previously listed diphenol precursors to the diglycidyl ethers containing a mesogenic or rodlike moiety; mixtures thereof and the like.

The epoxy resins which can be employed herein can be prepared by reacting the corresponding di- or polyhydroxyl containing compound (or amine containing compound) with an epihalohydrin by any suitable means known to those skilled in the art. Suitable such methods are disclosed by Lee and Neville in *Handbook of Epoxy Resins*, McGraw-Hill, (1967); Japan Kokai Tokkyo Koho JP 62 86,484 (87 96, 484); EP 88-008358/92 and Journal of Applied Polymer Science, Vol. 23, 1355–1372 (1972) all of which are incorporated herein by reference.

Generally, the di- or polyhydroxyl containing compound is reacted with an epihalohydrin in the presence of a suitable catalyst and in the presence or absence of a suitable solvent at a temperature suitably from about 0° C. to about 100° C., more suitably from about 20° C. to about 80° C., most suitably from about 20° C. to about 65° C.; at pressures suitably from about 30 mm Hg vacuum to about 100 psia., more suitably from about 30 mm Hg vacuum to about 50 psia., most suitably from about atmospheric pressure to about 20 psia.; for a time sufficient to complete the reaction, usually from about 1 to about 12, more usually from about 1 to about 5, most usually from about 1 to about 3 hours; and using from about 1.5:1 to about 100:1, preferably from about 2:1 to about 50:1, most preferably from about 3:1 to about 20:1 moles of epihalohydrin per hydroxyl group. This initial reaction unless the catalyst is an alkali metal or alkaline earth metal hydroxide employed in stoichiometric quantities produces a halohydrin intermediate which is then reacted with a basic acting compound to convert the vicinal chlorohydrin groups to epoxide groups. The resultant product is a glycidyl ether compound.

Suitable epihalohydrins which can be employed to prepare the epoxy resins useful in the present invention include, for example, those represented by the following formula

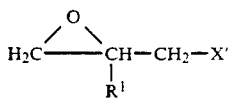

Formula XII wherein $R^1$ is as previously defined; and X' is a halogen. Particularly suitable such epihalohydrins include, for example, epichlorohydrin, epibromohydrin, epiiodohydrin, methylepichlorohydrin, methylepibromohydrin, methylepiiodohydrin, combinations thereof and the like.

Suitable di- or polyhydroxyl containing compounds (or amine containing compounds) which can be employed to prepare the epoxy resins useful in the present invention include, for example, those represented by the formulas

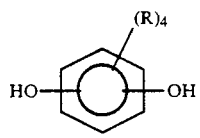

Formula XIII

-continued

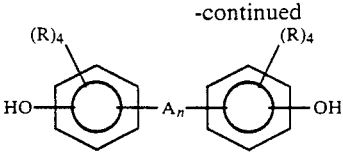

Formula XIV

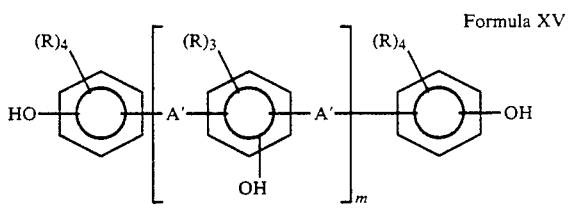

Formula XV

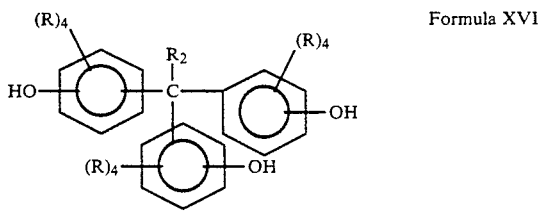

Formula XVI

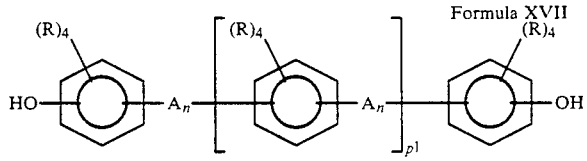

Formula XVII

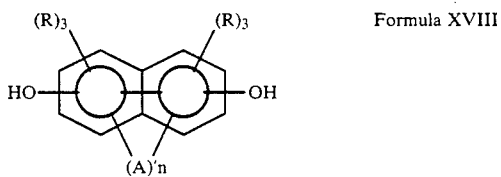

Formula XVIII

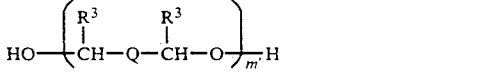

Formula XIX

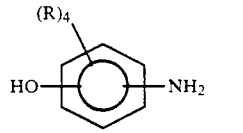

Formula XX

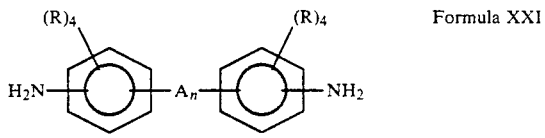

Formula XXI wherein R, $R^2$, $R^3$, Q, A, A', n, $p^1$, m and m' are as hereinbefore defined.

Suitable catalysts which can be employed to prepare the epoxy resins which can be employed herein include, for example, ammonium halides such as, for example, benzyltrimethylammonium chloride, benzyltrimethylammonium bromide, tetrabutylammonium chloride, tetrabutylammonium bromide, tetraoctylammonium chloride, tetraoctylammonium bromide, tetramethylammonium chloride, tetramethylammonium bromide, combinations thereof and the like.

Suitable basic acting compounds which can be employed to prepare the epoxy resins useful herein include, for example, alkali metal or alkaline earth metal hydroxides, carbonates, bicarbonates and the like. Particularly suitable such compounds include, for example, sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, lithium bicarbonate, calcium bicarbonate, barium bicarbonate, magnesium bicarbonate, manganese bicarbonate, mixtures, thereof and the like. Most preferred is sodium hydroxide or potassium hydroxide.

Suitable solvents which can be employed herein include, for example, alcohols, aliphatic hydrocarbons, aromatic hydrocarbons, glycol ethers, amides, sulfoxides, sulfones, combinations thereof and the like. Particularly suitable solvents include, for example, methanol, ethanol, isopropanol, hexane, heptane, octane, nonane, decane, toluene, xylene, ethylene glycol methyl ether, ethylene glycol ethyl ether, ethylene glycol n-butyl ether, ethylene glycol phenyl ether, propylene glycol methyl ether, propylene glycol phenyl ether, tripropylene glycol methyl ether, diethylene glycol methyl ether, diethylene glycol ethyl ether, diethylene glycol n-butyl ether, diethylene glycol phenyl ether, butylene glycol methyl ether, N,N-dimethylformamide, N-methylpyrrolidinone, N,N-dimethylacetamide, dimethylsulfoxide, sulfolane, combinations thereof and the like.

The solvent is usually employed in amounts suitably from about 5 to about 95, more suitably from about 20 to about 60, most suitably from about 30 to about 40, percent by weight based upon the combined weight of solvent and epihalohydrin.

For the production of epoxy resins from di- and polyhydroxyl containing compounds (or amine containing compounds) possessing functional groups or linkages that are sensitive to hydrolysis under the reaction conditions employed in certain of the epoxidation chemistries, alternate techniques of preparation may be employed. As a typical example, U.S. Pat. No. 4,762,901 teaches preparation of the diglycidyl ether of the biphenol represented by the following formula

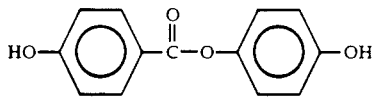

which is a compound containing an ester linkage known to be sensitive to hydrolysis, using an anhydrous epoxidation technique. This technique employs azeotropic removal of water/epichlorohydrin concurrent with the controlled addition of aqueous sodium hydroxide to a reaction mixture consisting of epichlorohydrin, a diphenol, a phase transfer catalyst such as, for example, benzyltrimethylammonium chloride, and optionally solvent(s). It is advantageous to conduct such anhydrous epoxidation reactions under a vacuum to facilitate the azeotropic removal of water. It is also operable and advantageous to utilize sodium hydroxide free of water as the alkali metal hydroxide reactant. In order to control reaction exotherm, the solid sodium hydroxide is typically added in aliquots as a powder to the epoxidation reaction mixture. A typical anhydrous epoxidation technique is described in U.S. Pat. No. 4,499,255 which is incorporated herein by reference in its entirety.

Another specific anhydrous epoxidation technique involves catalytic coupling of the di- or polyhydroxyl containing compound with an epihalohydrin, typically using as a catalyst one or more of the aforementioned ammonium halides. The resultant solution of halohydrin in excess epihalohydrin is then treated with finely pulverized potassium carbonate to effect dehydrohalogenation to the epoxy resin.

Advancement reaction of di- and polyglycidyl ethers can be performed by the known methods described in the aforementioned *Handbook of Epoxy Resins*. This usually includes combining one or more suitable compounds having an average of more than one active hydrogen atom per molecule, including, for example, dihydroxy aromatic, dithiol or dicarboxylic acid compounds or compounds containing one primary amine or amide group or two secondary amine groups and the di- or polyglycidyl ethers with the application of heat and mixing to effect the advancement reaction. A catalyst is frequently added to facilitate the advancement reaction.

The advancement of the epoxy resins containing one or more mesogenic or rodlike moieties with compounds having an average of more than one active hydrogen per molecule is employed to linearly chain extend the resin so as to produce an advanced epoxy resin. This linear chain extension is required for some mesogenic containing resin compositions in order to obtain liquid crystal character. The advancement of the mesogenic or rodlike epoxy resins can also be used to increase the temperature range in which a particular resin is liquid crystalline and to control the degree of crosslinking during the final curing stage.

The epoxy resin containing one or more mesogenic or rodlike moieties and the compound having an average of more than one active hydrogen atom per molecule are reacted in amounts which provide suitably from about 0.01:1 to about 0.99:1, more suitably from about 0.05:1 to about 0.9:1, most suitably from about 0.10:1 to about 0.50:1 active hydrogen atoms per epoxy group.

Particularly suitable compounds having an average of more than one active hydrogen atom per molecule which can be employed herein in the preparation of the advanced epoxy resins include hydroxyl-containing compounds, carboxylic acid-containing compounds and primary amine-containing compounds.

Particularly suitable hydroxyl-containing compounds include, for example, hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachlorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, bis(N,N'-4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1''-carboxy)-biphenyl, mixtures thereof and the like.

Particularly suitable carboxylic acidcontaining compounds include, for example, terephthalic acid, 4,4'-benzanilide dicarboxylic acid, 4,4'-phenylbenzoate dicarboxylic acid, 4,4'-stilbenedicarboxylic acid and mixtures thereof and the like.

Particularly suitable primary amine-containing compounds include, for example, aniline, 4'-sulfonamido-N-phenyl benzamide, 4'-sulfonamido-N'-phenyl-4-chlorobenzamide, 4-amino-1-phenylbenzoate, 4-amino-N-phenylbenzamide, N-phenyl-4-amino-phenyl-1-carboxamide, phenyl-4-aminobenzoate, biphenyl-4-aminobenzoate, 1-phenyl-4'-aminophenylterephthalate, mixtures thereof and the like.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate-acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate-acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216; and 4,366,295, all of which are incorporated herein by reference.

The amount of advancement catalyst depends, of course, upon the particular reactants and catalyst employed; however, it is usually employed in quantities of from about 0.03 to about 3, preferably from about 0.03 to about 1.5, most preferably from about 0.05 to about 1.5 percent by weight based upon the weight of the epoxy containing compound.

The advancement reaction can be conducted at atmospheric, superatmospheric or subatmospheric pressures at temperatures of from about 20° C. to about 260°0 C., preferably from about 80° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. For the production of advanced epoxy resins using a reactant which is of low solubility in the di- or polyglycidyl ether reactant, it is frequently of advantage to add one or more solvents to the reaction mixture. Suitable such solvents include, for example, glycol ethers, aliphatic and aromatic hydrocarbons, aliphatic ethers, cyclic ethers, ketones, esters, amides, combinations thereof and the like. Particularly suitable solvents include, for example, toluene, benzene, xylene, methyl ethyl ketone, methyl isobutyl ketone, diethylene glycol methyl ether, dipropylene glycol methyl ether, dimethylformamide, dimethylsulfoxide, N-methypyrrolidinone, tetrahydrofuran, propylene glycol methyl ether, combinations thereof and the like. The solvents can be employed in amounts of from about zero to about 80%, preferably from about 20% to about 60%, more preferably from about 30% to about 50% by weight based upon the weight of the reaction mixture. Care should be taken to utilize only those solvents which are inert to reaction with any of the reactants employed in the advancement reaction or the product formed therefrom.

THERMOSETTABLE (CURABLE) MIXTURES

The thermosettable mixtures of the present invention are prepared by mixing together one or more diaminoalpha-alkylstilbene compositions with one or more epoxy resins, all, none, or a part of which may contain one or more mesogenic moieties. The diaminoalphaalkylstilbene compositions are employed in amounts which will effectively cure the mixture, with the understanding that these amounts will depend upon the particular diamino-alpha-alkylstilbene and epoxy resin employed. Generally, suitable amounts of the adduct include amounts which will provide from about 0.80:1 to about 1.50:1 equivalents of amine hydrogen in the diamino-alpha-alkylstilbene which is reactive with an epoxide group per equivalent of epoxide group in the epoxy resin at the conditions employed for curing.

A preferred thermosettable mixture of the present invention comprises a curing amount of one or more 4,4'-diamino-alpha-alkylstilbenes or N,N'-dialkyl-4,4'-diamino-alpha-alkylstilbenes with one or more epoxy resins containing one or more mesogenic moieties. Most preferred as the thermosettable mixture of the present invention is a curing amount of 4,4'-diamino-alphamethylstilbene and/or N,N'-dimethyl-4,4'-diaminoalphamethylstilbene with the diglycidyl ether of 4,4'-dihydroxy-alpha-methylstilbene.

The application of heat or a combination of heat and pressure may be employed in the curing of the thermosettable mixtures of the present invention. Temperatures employed can vary over a considerable range but are usually in the range of 20° C. to 250° C. Depending upon the relative solubility and phase transition temperature(s) associated with the mesogenic moieties present in the thermosettable compositions, curing at an elevated temperature can be especially desirable to enhance the molecular anisotropy of the cured product.

The thermosettable mixtures of the present invention may also contain one or more of the known curing agents for epoxy resins such as, for example, primary and secondary polyamines, carboxylic acids and anhydrides thereof, aromatic hydroxyl containing compounds, imidazoles, guanidines, urea-aldehyde resins, alkoxylated urea-aldehyde resins, melamine-aldehyde resins, alkoxylated melamine-aldehyde resins, aliphatic polyamines, cycloaliphatic, polyamines, aromatic polyamines, epoxy resin adducts, all, none, or a part of which may contain one or more mesogenic moieties, combinations thereof and the like. Particularly suitable curing agents include, for example, methylenedianiline, 4,4'-diaminostilbene, 4,4'-diaminobenzanilide, 4,4'-diamino-alphachlorostilbene, dicyandiamide, ethylenediamine, diethylenetriamine, triethylenetetramine, tetraethylenepentamine, urea-formaldehyde resins, melamine-formaldehyde resins, methylolated ureaformaldehyde resins, methylolated melamine-formaldehyde resins, phenol-formaldehyde novolac resins, sulfanilamide, diaminodiphenylsulfone, diethyltoluenediamine, t- butyltoluenediamine, bis-4-aminocyclohexylmethane, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like. If used as a component of the thermosettable mixtures of the present invention, from about 1 to about 99, preferably from about 1 to about 40, most preferably from about 1 to about 20 percent of the equivalents of amine hydrogen which are reactive with an epoxide group provided by the diamino-alpha-alkylstilbene are substituted by using one or more of the aforesaid curing agents.

ORIENTATION

During processing prior to curing and/or during cure of the curable epoxy resin compositions into a part, electric or magnetic fields or shear stresses can be applied for the purpose of orienting the mesogenic or rodlike moieties contained or developed therein which in effect improves the mechanical properties. As specific examples of these methods, Finkelmann, et al, *Macromol. Chem.*, 180, 803–806 (March 1979) induced orientation in thermotropic methacrylate copolymers containing mesogenic side chain groups decoupled from the main chain via flexible spacers in an electric field. Orientation of mesogenic side chain groups decoupled from the polymer main chain via flexible spacers in a magnetic field has been demonstrated by Roth and Kruecke, *Macromol. Chem.*, 187, 2655–2662 (November 1986). Magnetic field induced orientation of mesogenic main chain containing polymers has been demonstrated by Moore, et al, *ACS Polymeric Material Sciences and Engineering*, 52, 84–86 (April-May 1985). Magnetic and electric field orientation of low molecular weight mesogenic compounds is discussed by W. R. Krigbaum in *Polymer Liquid Crystals*, pages 275–309 (1982) published by Academic Press, Inc. All of the above are incorporated herein by reference in their entirety.

In addition to orientation by electric or magnetic fields, polymeric mesophases can be oriented by drawing and/or shear forces which are induced by flow through dies, orifices, and mold gates. A general discussion for orientation of thermotropic liquid crystal polymers by this method is given by S. K. Garg and S. Kenig in *High Modulus Polymers*, pages 71–103 (1988) published by Marcel Dekker, Inc. which is incorporated herein by reference. For the mesomorphic systems based on the epoxy resin compositions, this shear orientation can be produced by processing methods such as injection molding, extrusion, pultrusion, filament winding, filming and prepreging.

The thermosettable mixtures of the present invention can be blended with other materials such as solvents or diluents, fillers, pigments, dyes, flow modifiers, thickeners, reinforcing agents, mold release agents, wetting agents, stabilizers, fire retardant agents, surfactants, combinations thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended composition.

Solvents or diluents which can be employed herein include, for example, hydrocarbons, ketones, glycol ethers, aliphatic ethers, cyclic ethers, esters, amides, monoepoxides, combinations thereof and the like. Particularly suitable solvents or diluents include, for example, toluene, benzene, xylene, methyl ethyl ketone, methyl isobutyl ketone, diethylene glycol methyl ether, dipropylene glycol methyl ether, dimethylformamide, N-methylpyrrolidinone, tetrahydrofuran, propylene glycol methyl ether, 4-tertiary-butylphenyl glycidyl ether, cresyl glycidyl ether, epoxidized soybean oil, combinations thereof and the like.

The modifiers such as thickeners, flow modifiers and the like can be suitably employed in amounts of from zero to about 10, more suitably from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers of whiskers, hollow spheres, and the like. Suitable reinforcing materials include, glass, ceramics, nylon, rayon, cotton, aramid, graphite, polyalkylene terephthalates, polyethylene, polypropylene, polyesters, combinations thereof and the like.

Suitable fillers which can be employed herein include, for example, inorganic oxides, ceramic microspheres, plastic microspheres, glass microspheres, inorganic whiskers, $CaCO_3$, combinations thereof and the like.

The fillers can be employed in amounts suitable from about zero to about 95, more suitably from about 10 to about 80, most suitably from about 40 to about 60 percent by weight based upon the weight of the total composition.

The compositions of the present invention are useful in, but not limited to, applications such as coatings, encapsulations, extrusions, moldings, pultrusions, electrical and structural laminates or composites, and the like. In some instances, they can be formed into monofilament and multifilament fibers.

The following examples are illustrative of the present invention, but are not to be construed as to limiting its scope in any manner.

EXAMPLE 1

A. Synthesis of 4,4'-Dihydroxy-alpha-methylstilbene

Phenol (752.8 grams, 8.0 moles), chloroacetone (384.7 grams, 4.0 moles as chloroacetone) and methylene chloride (600 grams) are added to a reactor and cooled to −10° C. with stirring under a nitrogen atmosphere. The chloroacetone used is a commercial grade containing 96.25% chloroacetone, 0.05% acetone, 3.05% 1,1-dichloroacetone and 0.60% mesityl oxide. Concentrated sulfuric acid (392.32 grams, 4.0 mole) is added dropwise to the stirred solution over a forty five minute period and so as to maintain the reaction temperature between −11° and −9° C. After 150 minutes of post reaction at −11° to −9° C., the viscous, orange colored oil product is mixed with iced deionized water (1000 milliliters). The oil product is separated then washed with a second portion (1000 milliliters) and then a third portion (1000 milliliters) of deionized water. After separation, the recovered oil product is added to a pair of 2 liter beakers along with ethanol (250 milliliters) and stirred to provide solutions. Deionized water (250 milliliters) is added to the stirred solutions and heating commences. As the temperature of the mixture increases, the stirred mixtures began to clear. Each time clearing is observed, sufficient deionized water is added to induce cloudiness, followed by continuation of the mixing and heating. Once the temperature reaches 90° C., a massive precipitation of white crystalline plates occurs and is followed by immediate coalesence of the precipitated product to an oil. The oil layer is recovered by decantation of the water layer and ethanol (250 milliliters) is added. Deionized water is again added to the stirred solutions as heating commences, in an amount sufficient to induce cloudiness each time clearing is observed. Once the temperature reaches 70° C., a massive precipitation of white crystalline plates again occurs. At this time, stirring is stopped, sufficient deionized water is added to fill both of the beakers and the crystalline slurries are chilled to 4° C. and held therein for 16 hours. The crystalline product is recovered by filtration of the chilled crystalline slurries, added to a beaker along with deionized water (1000 milliliters), then stirred with heating to 100° C. After maintaining the stirred slurry at 100° C. for thirty minutes, the crystalline product is recovered by filtration then again combined with deionized water (1000 milliliters) and stirred with heating to 100° C. The crystalline product is recovered by filtration then dried in a vacuum oven at 100° C. and 5 mm Hg to a constant weight of 478.8 grams. Proton magnetic resonance spectroscopy and Fourier transform infrared spectrophotometric analysis confirms the product structure.

B. Synthesis of bis(4-Aryloxy-2-phenylquinazoline) of 4,4'-Dihydroxy-alpha-methylstilbene 4,4'-Dihydroxy-alpha-methylstilbene (11.31 grams, 0.10 hydroxyl equivalent) from A above and 1,4-dioxane (150 milliliters) are added to a reactor and stirred at 24° C. under a nitrogen atmosphere to provide a solution. Sodium (2.41 grams, 0.105 mole) is added as pieces, then heating of the stirred suspension commences. After 40 minutes, the reaction temperature reaches 100° C. with vigorous reaction resulting. After 109 minutes at the 100° C. temperature complete dissolution of the sodium has occurred accompanied by formation of a slurry of tan needles of the bis(sodium phenate) of 4,4'-dihydroxy-alpha-methylstilbene. The reactor is cooled to 21° C. over the next 91 minutes followed by the addition of 4-chloro-2-phenylquinazoline (24.07 grams, 0.10 mole) over a five minute period. Heating of the slurry commences over the next 41 minutes until a vigorous refluxing solution (100° C.) is obtained. After 56 minutes under refluxing conditions, cooling of the solution commences. As the temperature reaches 78° C., a thick, light tan colored crystalline slurry forms. The slurry is diluted at this time with isopropanol (100 milliliters), then recovered and poured into a beaker of deionized water (500 milliliters). After stirring of the deionized water slurry for five minutes, the crystalline product is recoverd by filtration, then washed with three portions (250 milliliters) of deionized water. The recovered wet product is boiled in 5% weight deionized water/95% weight ethanol (600 milliliters) then allowed to cool under ambient conditions to room temperature (22° C.). The resulting crystalline precipitate is recovered by filtration then dried in a vacuum oven at 100° C. and 5 mm Hg to a constant weight of 22.9 grams of creme colored crystals. Fourier transform infrared spectrophotometric analysis of a potassium bromide pellet of the product confirms the product structure: 3064 and 3031 cm$^{-1}$ C—H stretching absorbances of aromatic rings and =C—H; 1623 cm$^{-1}$ C=N stretching absorbance; 1596, 1576, 1556, 1510 and 1489 cm$^{-1}$ absorbances in the C=C stretching region; and 932, 852, 773 and 706 cm$^{-1}$ ring substitution absorbances. Differential scanning calorimetry of a portion (11.7 milligrams) of the product under a stream of nitrogen flowing at 35 cubic centimeters per minute and using a heating rate of 10° C. per minute with a range of 25° C. to 400° C. reveals a sharp melting point endotherm centered at 214.5° C. (enthalpy=58.7 joules per gram). After melting, a gradual exothermic shift from the baseline onset at 269° C. with a sharp exothermic shift commencing at 363.5° C.

C. Rearrangement Reaction of the bis(4-Aryloxy-2-phenylquinazoline) of 4,4'-Dihydroxy-alphamethylstilbene to the bis(3-Aryl-2-phenyl-4(3H)quinazolinone A portion (10.0 grams) of the bis(4-aryloxy-2-phenylquinazoline) of 4,4'-dihydroxy-alphamethylstilbene from B above is added to a reactor and stirred under a nitrogen atmosphere with heating. After 14 minutes, a reaction temperature of 325° C. is achieved and is maintained between 321° and 329° C. for the next 130 minutes. At this time, a sample of the reaction product is removed and analyzed by Fourier transform infrared spectrophotometric analysis, revealing that complete conversion of the quinazoline to the quinazolinone has occurred. After an additional 23 minutes between 321° and 329° C., the reaction product is cooled to room temperature (22° C.) and recovered as a brittle, transparent brown solid. Fourier transform infrared spectrophotometric analysis of a potassium bromide pellet of the product confirms the product structure: 3064 and 3037 cm$^{-1}$ C—H stretching absorbances of aromatic rings and =C—H; 1689 cm$^{-1}$ ketone C=O stretching absorbance; 1609, 1589, 1563, 1510, 1497 and 1470 cm$^{-1}$ absorbances in the C=C stretching region; and 766, 699 and 647 cm$^{-1}$ ring substitution absorbances.

D. Synthesis of 4,4'-Diamino-alpha-methylstilbene

A portion (8.0 grams) of the bis(3-aryl-2-phenyl-4(3H)quinazolinone from C above is ground to a fine powder and added to a reactor along with potassium hydroxide (32.0 grams) and ethylene glycol (175 milliliters). Stirring under a nitrogen atmosphere commences with heating. Once the reaction temperature reaches 128° C., a solution forms. Heating continues to 130° C. and is held therein for the next 39.5 hours. The reactor is cooled to 80° C. and the contents added to a beaker containing stirred deionized water (1000 milliliters). After the stirred slurry has cooled to room temperature (23° C.) it is added to a separatory funnel and extracted with three portions (250 milliliters) of diethyl ether. The combined ether extract is dried over anhydrous sodium sulfate then filtered to provide a solution. Anhydrous hydrogen chloride gas is sparged into the dry ether solution until a precipitate is obtained, followed by sparging with dry nitrogen. The precipitate is allowed to settle followed by decantation through a filter to remove the ether plus any unsettled precipitate. The precipitate is dissolved in deionized water (400 milliliters) then neutralized by addition of 10 percent weight aqueous sodium hydroxide solution to a pH of 12. The resulting precipitate is recovered by filtration, then washed with two portions (50 milliliters) of deionized water. The washed product is dried in a vacuum oven at 50° C. and 5 mm Hg to a constant weight of 1.57 grams of light brown colored powder. Fourier transform infrared spectrophotometric analysis of a potassium bromide pellet of the product confirms the product structure: 3428, 3376 and 3216 [minor] cm$^{-1}$ N—H stretching absorbances of —NH$_2$ groups; 3031 cm$^{-1}$ C—H stretching absorbance of aromatic rings and =C—H; 2957 and 2924 cm$^{-1}$ C—H stretching absorbances; 1616 cm$^{-1}$ —NH$_2$ deformation; 1609 [shoulder] cm$^{-1}$ absorbance in the C=C stretching region; 1516 cm$^{-1}$ aromatic ring C=C stretching absorbance; 1384 cm$^{-1}$ symmetric C—H bending in the —CH$_3$ group; 1271 cm$^{-1}$ aromatic ring carbonnitrogen stretching absorbance; and 832 cm$^{-1}$ para ring substitution absorbance (may be overlapping with R$_2$C=CHR deformation).

Gas chromatography-mass spectrometry (GC-MS) is completed by dissolving a portion of the product in methanol and injecting a 0.5 microliter sample of the solution into a Finnigan 4023 GC-MS using the following column and conditions: 60 M×0.25 mm, 1 µ DB-5 (102121) fused silica capillary column, 290° C. isothermal, I=S=T=250° C., 30 lb. helium flow, 60 cubic centimeter per minute injection split. A pair of 4,4'-diamino-alphamethylstilbene isomers are resolved on the column and collectively comprise in excess of 80 percent of the sample. Mass spectra of these isomers provides the expected molecular ion and base peak at m/z=224 amu. A minor component resolved on the column comprises less than 20 percent of the sample. The mass spectrum of this minor component provides a molecular ion at m/z=226 amu and a base peak at m/z=120 amu. The minor component is tentatively identified as 1,2-(4,4'-diaminophenyl)propane.

EXAMPLE 2

A. Epoxidation of 4,4'-Dihydroxy-alpha-methylstilbene 4,4'-Dihydroxy-alpha-methylstilbene (452.5 grams, 4.0 hydroxyl equivalents) from Example 1-A, epichlorohydrin (1850.6 grams, 20.0 moles), deionized water (160.9 grams, 8.0 percent by weight of the epichlorohydrin used) and isopropanol (996.5 grams, 35 percent by weight of the epichlorohydrin used) are added to a reactor and heated to 50° C. with stirring under a nitrogen atmosphere. Once the 50° C. reaction temperature is achieved, sodium hydroxide (144.0 grams, 3.60 moles) dissolved in deionized water (576.0 grams) is added dropwise to the reactor over a 45 minute period and so as to induce an exothermic increase in temperature to 59° C., with subsequent maintenance of the temperature at 55° C. Ten minutes after completion of the aqueous sodium hydroxide addition, the stirring is stopped and the aqueous layer which separates from the reaction mixture is pipetted off and discarded. Stirring is resumed and after a total of twenty minutes following completion of the initial aqueous sodium hydroxide addition, a second solution of sodium hydroxide (64.0 grams, 1.60 mole) dissolved in deionized water (256.0 grams) is added to the reactor over a twenty minute period with maintenance of the 55° C. reaction temperature. Fifteen minutes after completion of the aqueous sodium hydroxide addition, the recovered reaction mixture is added to a separatory funnel and washed with 1500 milliliters of deionized water. The separated organic layer is washed a second time (1500 milliliters deionized water), recovered and then rotary evaporated under vacuum to final conditions of 150° C. and 1 mm Hg for 120 minutes. The product is recovered (652.31 grams) as an off-white, crystalline solid. Recrystallization is completed by stirring the solid product in acetone (710 grams) maintained at reflux (58° C.) for two hours. The slurry is cooled to room temperature (24° C.) and filtered after 16 hours followed by drying in a vacuum oven at 70° C. and. 2 mm Hg to a constant weight of 503.0 grams of crystalline white diglycidyl ether of 4,4'-dihydroxy-alpha-methylstilbene having an epoxide equivalent weight (EEW) of 176.86.

B. Characterization of the Diglycidyl Ether of 4,4'-Dihydroxy-alpha-methylstilbene for Liquid Crystallinity Analysis of the diglycidyl ether from A above via crosspolarized light microscopy is completed using a microscope equipped with a programmable hot stage using a heating rate of 10° C. per minute. The results are reported in Table I.

TABLE I

| Cycle Designation | Observed Transition Temperatures (°C.) | Comments |
|---|---|---|
| First heating | 30 | White, opaque, birefringent solid. |
| | 115 | First melting noted. |
| | 133 | Isotropization complete. |
| First cooling | 140 | Isotropic fluid. |
| | 100 | Nematic liquid crystal texture forms. |
| | 60 | First crystallization noted. |

The diglycidyl ether is a monotropic liquid crystal with a nematic texture observed in the microscopic analysis.

C. Microscopic Observations During the Cure of the Diglycidyl Ether of 4,4'-Dihydroxy-alpha-methylstilbene with 4,4'-Diamino-alpha-methylstilbene A portion of the diglycidyl ether of 4,4'-dihydroxy-alpha-methylstilbene (0.1284 gram) from A above is combined with a stoichiometric equivalent amount of 4,4'-diamino-alpha-methylstilbene (0.0407 gram) from Example 1-D and dissolved in methylene chloride (3 milliliters) to form a homogeneous solution. After evaporation of the methylene chloride solvent under a stream of nitrogen, a sample of the resulting powder mixture between glass slides is placed on a heated stage. Heating commences at a rate of 10° C. per minute concurrent with observation of the sample at 70X magnification using an optical microscope and a crosspolarized light source. At 64° C., the first birefringent fluidity is observed as the sample is compressed between the two glass slides. At 76° C., a birefringent fluid is obtained. At 124° C., isotropization is complete. At 177° C., gelation occurs followed by thermosetting to a non-birefringent solid at 183° C. The solid thus produced becomes highly birefringent when scratched with a steel needle or rubbed between the two glass slides.

A second portion of the powder mixture between glass slides is placed on a stage which has been preheated to 160° C. After 8 seconds at the 160° C. temperature, an isotropic melt is formed and cooling commences. After an additional forty six seconds, the temperature reaches 140° C. and is held therein. After a total of five minutes has elapsed, initial shear induced birefringence is observed in the 140° C. resin concurrent with increase in viscosity. After a total of six minutes and forty five seconds has elapsed, thermosetting to solid possessing birefringence where shear has been previously applied occurs. Further heating to 200° C. at a rate of 10° C. per minute has no visually observable effect on the ordered morphology produced at the 140° C. temperature.

A third portion of the powder between glass slides is placed on a stage which has been preheated to 160° C. After 8 seconds at the 160° C. temperature, an isotropic melt is formed. After an additional 52 seconds at the 160° C. temperature, the glass slides containing the sample are removed and allowed to cool. A fluid is thus obtained which becomes opalescent upon stirring and possesses a nematic texture.

D. Preparation of a Casting of the Diglycidyl Ether of 4,4'-Dihydroxy-alpha-methylstilbene Cured with 4,4'-Diamino-alpha-methylstilbene and Analysis by Differential Scanning Calorimetry The portion of the diglycidyl ether of 4,4'-dihydroxy-alpha-methylstilbene and 4,4'-diamino-alphamethylstilbene powder mixture remaining from C above is contained in an aluminum pan and placed in an oven preheated to 150° C. After one hour at 150° C., the oven temperature is increased to 200° C. and the resin held therein for the next hour. The oven temperature is increased 230° C. and held therein for two hours, followed by cooling to room temperature (23° C.). At room temperature, a transparent, light amber colored casting is removed from the aluminum pan. A sample of the casting (12 milligrams) is analyzed via differential scanning calorimetry. A first heating to 290° C. is completed at a rate of 20° C. per minute under a stream of nitrogen flowing at 35 cubic centimeters per minute, with the sample held therein for twenty minutes before cooling to 30° C. A second heating is completed using a heating rate of 10° C. per minute and a temperature range of 30° to 400° C. under a stream of nitrogen flowing at 35 cubic centimeters per minute. At 320° C. and below, no residual cure energy and no glass transition temperature are observed. Above 320° C., the onset to exothermic decomposition occurs with a maximum observed at 355° C.

What is claimed is:

1. A curable composition comprising
(A) a curing amount of one or more diamino-alphaalkylstilbenes represented by the following Formula I

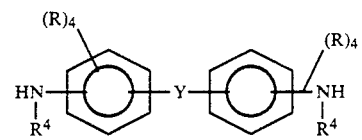

Formula I wherein each R is independently hydrogen or a hydrocarbyl or hydrocarbyloxy group having from 1 to about 10 carbon atoms, a halogen atom, a nitro group, a nitrile group or a —CO—$R^1$ group; each $R^1$ is independently hydrogen or a hydrocarbyl group having from 1 to about 3 carbon atoms; each $R^4$ is independently hydrogen or a hydrocarbyl group having from 1 to about 10 carbon atoms; Y is a

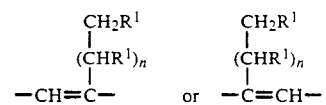

group and n has a value of zero or one;
(B) one or more epoxy resins; and
(C) one or more curing agents for epoxy resins other than those of component (A) in an amount such that from about 1 to about 99 percent of the equivalents of amine hydrogen which are reactive with an epoxide group provided by the diamino-alphaalkylstilbene of component (A) are substituted by using one or more of the aforesaid curing agents of this component (C).

2. A curable composition of claim 1 wherein in component (A) when R is a hydrocarbyl or hydrocarbyloxy group, it has from 1 to about 4 carbon atoms; when $R^1$ is a halogen, it is chlorine or bromine; and when $R^4$ is a hydrocarbyl group, it has from 1 to about 6 carbon atoms; and component (B) is an epoxy resin represented by the following Formulas III, IV, V, VI, VII, VIII, IX, X or XI

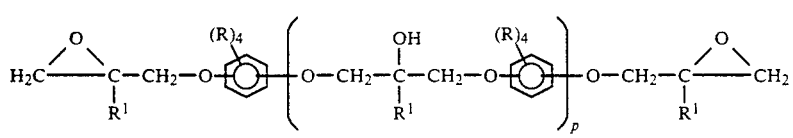

Formula III

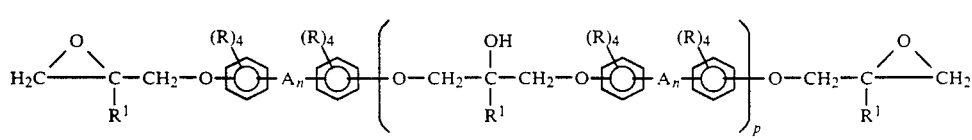

Formula IV

-continued

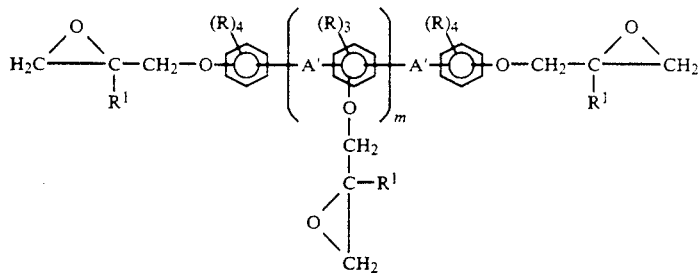

Formula V

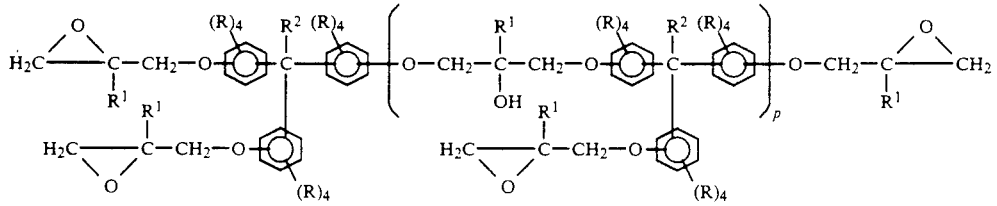

Formula VI

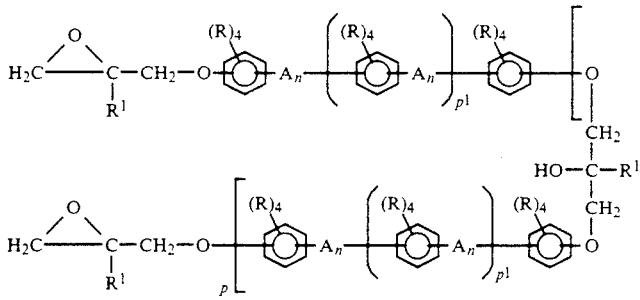

Formula VII

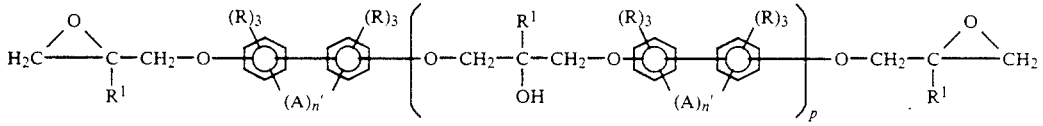

Formula VIII

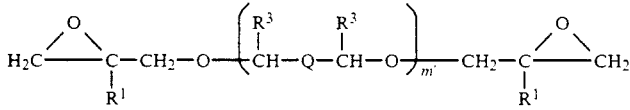

Formula IX

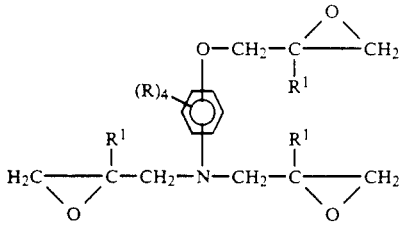

Formula X

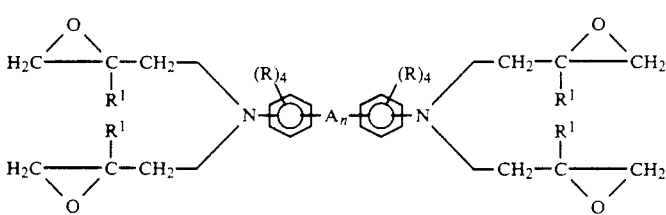

Formula XI wherein each A is independently selected from the group consisting of a direct single bond, a divalent saturated aliphatic hydrocarbyl group having from 1 to about 20 carbon atoms, —O—, —CO—, —SO—, —SO$_2$—, —S—, —S—S—, —CR$^1$=CR$^1$—, —C≡C—, —N=N—, —CR$^1$=N—, —O—CO—, —NR$^1$—CO—, —CR$^1$=N—N=CR$^1$—, —CR$^1$=CR$^1$—CO—, —N=CR$^1$—, —CO—O—, —CO—NR$^1$—, —CO—CR¹=CR¹—, —CO—O—N=CR¹, —CR¹=N—O—OC—, —CO—NR¹—NR¹—OC—, —CR¹=CR¹—O—OC—, —CO—O—CR¹=CR¹—, —O—OC—CR¹=CR¹—, —CR¹=CR¹—CO—O—, —(CHR¹)ₙ'—O—CO—CR¹=CR¹—, —CR¹=CR¹—CO—O—(CHR¹)ₙ'—, —(CHR¹)ₙ'—CO—O—CR¹=CR¹—, —CR¹=CR¹—O—CO—(CHR¹)ₙ'—, —CO—S—, —S—OC—, —CH₂—CH₂—CO—O—, —O—OC—CH₂—CH₂—, —C≡C—C≡C—, —CR¹=CR¹—CR¹=CR¹—,

[structures]

each A' is independently a divalent hydrocarbyl group having from 1 to about 10 carbon atoms; each A¹ is independently a $$-\overset{O}{\underset{\|}{C}}-, \quad -O-\overset{O}{\underset{\|}{C}}-, \quad -\overset{O}{\underset{\|}{C}}-O-, \quad -\overset{O}{\underset{\|}{C}}-NR^1-, \text{ or}$$

$$-NR^1-\overset{O}{\underset{\|}{C}}- \text{ group;}$$

each R is independently hydrogen or a hydrocarbyl or hydrocarbyloxy group having from 1 to about 10 carbon atoms, a halogen atom, a nitro group, a nitrile group or a —CO—R¹ group; each R¹ is independently hydrogen or a hydrocarbyl group having 1 to about 3 carbon atoms; each R² is independently hydrogen or a hydrocarbyl group having from 1 to about 10 carbon atoms or a halogen atom; each R³ is independently hydrogen or a hydrocarbyl or halohydrocarbyl group having from 1 to about 6 carbon atoms; Q is a direct bond, —CH₂—S—CH₂—, —(CH₂)ₙ''—, or

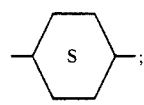

m has a value from about 0.001 to about 6; m' has a value from 1 to about 10; n" has an average value from about 1 to about 10; n is zero or 1; n' has a value from 1 to about 6; p has a value from zero to about 30; $p^1$ has a value from 1 to about 30.

3. A curable composition of claim 2 wherein component (A) is a 4,4'-diamino-alpha-alkylstilbene or a N,N'-dialkyl-4,4'-diamino-alpha-alkylstilbene and component (B) is a mesogenic epoxy resin represented by the following Formulas IV, VII, VIII or XI

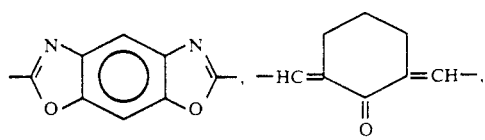

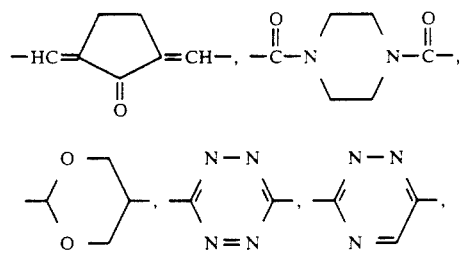

Formula IV

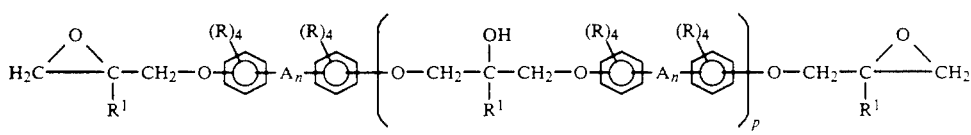

Formula VII

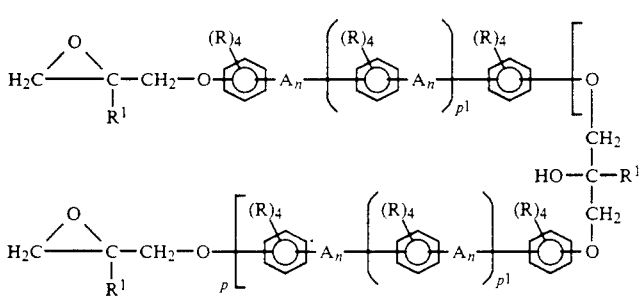

Formula VIII

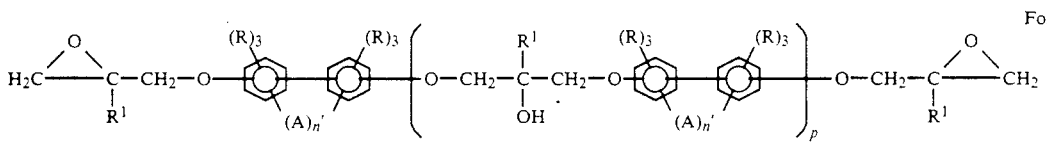

Formula XI

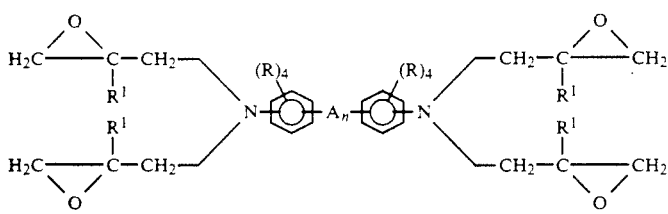

wherein each A is independently selected from the group consisting of a direct single bond, $-CR^1=CR^1-$, $-C\equiv C-$, $-N=N-$, $-CR^1=N-$, $-O-CO-$, $-NR^1-CO-$, $-CR^1=N-N=CR^1-$, $-CR^1=CR^1-CO-$, $-N=CR^1-$, $-CO-O-$, $-CO-NR^1-$, $-CO-CR^1=CR^1-$, $-CO-O-N=CR^1$, $-CR^1=N-O-OC-$, $-CO-NR^1-NR^1-OC-$, $-CR^1=CR^1-O-OC-$, $-CO-O-CR^1=CR^1-$, $-O-OC-CR^1=CR^1-$, $-CR^1=CR^1-CO-O-$, $-(CHR^1)_{n'}-O-CO-CR^1=CR^1-$, $-CR^1=C-R^1-CO-O-(CHR^1)_{n'}-$, $-(CHR^1)_{n'}-CO-O-CR^1=CR^1-$, $-CR^1=C-R^1-O-CO-(CHR^1)_{n'}-$, $-CO-S-$, $-S-OC-$, $-CH_2-CH_2-CO-O-$, $-O-OC-CH_2-CH_2-$, $-C\equiv C-C\equiv C-$, $-CR^1=CR^1-CR^1=CR^1-$,

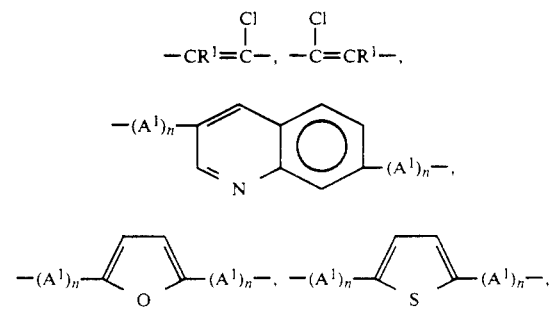

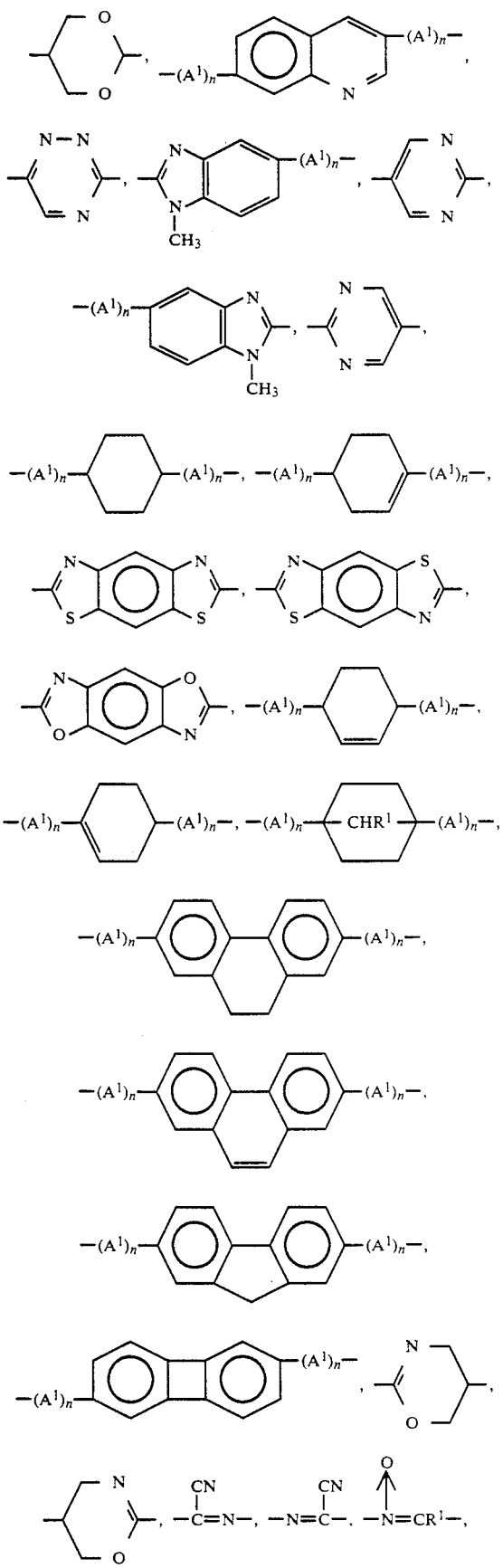

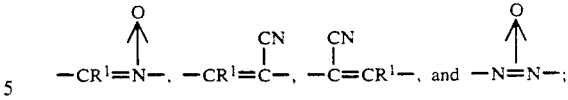

each A' is independently a divalent hydrocarbyl group having from 1 to about 10 carbon atoms; each $A^1$ is independently a

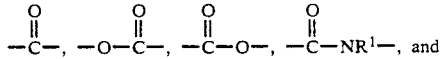

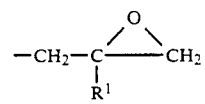  group;

each R is independently hydrogen or a hydrocarbyl or hydrocarbyloxy group having from 1 to about 10 carbon atoms, a halogen atom, a nitro group, a nitrile group, or a —CO—$R^1$ group; each $R^1$ is independently hydrogen or a hydrocarbyl group having 1 to about 3 carbon atoms; n is zero or 1; n' has a value from 1 to about 6; p has a value from zero to about 30; $p^1$ has a value from 1 to about 30; with the proviso that at least 80% of the molecules are para substituted by the bridging groups (—A— in Formulas IV, VII, XI and by the direct bond in Formula VIII), the substituent containing the glycidyl group(s), $$-CH_2-\underset{R^1}{C}-CH_2$$
   (with epoxide O)

and the substituent containing the secondary hydroxy alkylidene group(s), —$CH_2$—C(OH)($R^1$)—$CH_2$—, which are present when p or $p^1$ has a value greater than zero.

4. A curable composition of claim 1 wherein component (C) is selected from the group consisting of primary and secondary polyamines, carboxylic acids and anhydrides thereof, aromatic hydroxyl containing compounds, imidazoles, guanidines, urea-aldehyde resins, alkoxylated urea-aldehyde resins, melamine-aldehyde resins, alkoxylated melamine-aldehyde resins, aliphatic polyamines other than said primary and secondary polyamines, cycloaliphatic polyamines other than said primary and secondary polyamines, aromatic polyamines other than said primary and secondary polyamines, and epoxy resin adducts, all, none, or a part of which may contain one or more mesogenic moieties and combinations thereof; and is present in an amount such that from about 1 to about 40 percent of the equivalents of amine hydrogen which are reactive with an epoxide group provided by the diamino-alpha-alkylstilbene are substituted by using one or more of the component (C).

5. The product resulting from curing a curable composition of claim 1.

6. The product resulting from curing a curable composition of claim 4.

7. A curable composition of claim 2, 3, 1 or 4 which has been oriented prior to or during curing.

8. A curable composition of claim 7 wherein said orientation is accomplished by means of the application of an electric or magnetic field, drawing or shear forces or any combination thereof.

9. The product resulting from curing a curable composition of claim 7.

10. The product resulting from curing a curable composition of claim 8.

* * * * *